US012508159B2

(12) United States Patent
Meyer et al.

(10) Patent No.: US 12,508,159 B2
(45) Date of Patent: Dec. 30, 2025

(54) ARRANGEMENT FOR MODIFYING AN INTERNAL EYE PRESSURE IN VIVO

(71) Applicant: IMPLANDATA OPHTHALMIC PRODUCTS GMBH, Hannover (DE)

(72) Inventors: Stefan Meyer, Hannover (DE); Max Ostermeier, Seevetal (DE)

(73) Assignee: IMPLANDATA OPHTHALMIC PRODUCTS GMBH, Hannover (DE)

(*) Notice: Subject to any disclaimer, the term of this patent is extended or adjusted under 35 U.S.C. 154(b) by 644 days.

(21) Appl. No.: 17/714,767

(22) PCT Filed: Oct. 5, 2020

(86) PCT No.: PCT/EP2020/077795
§ 371 (c)(1),
(2) Date: Apr. 6, 2022

(87) PCT Pub. No.: WO2021/069352
PCT Pub. Date: Apr. 15, 2021

(65) Prior Publication Data

US 2023/0024140 A1 Jan. 26, 2023

(30) Foreign Application Priority Data

Oct. 8, 2019 (DE) ......................... 102019126959.8

(51) Int. Cl.
*A61F 9/007* (2006.01)
*A61B 3/16* (2006.01)
*A61F 9/00* (2006.01)

(52) U.S. Cl.
CPC ............ *A61F 9/00781* (2013.01); *A61B 3/16* (2013.01); *A61F 9/0017* (2013.01); *A61F 2250/0067* (2013.01)

(58) Field of Classification Search
CPC ................ A61F 9/00781; A61F 9/0017; A61F 2250/0067; A61F 2250/0002;
(Continued)

(56) References Cited

U.S. PATENT DOCUMENTS

2002/0049389 A1* 4/2002 Abreu .................. A61B 3/0058
600/318
2003/0225318 A1* 12/2003 Montegrande ....... A61B 5/0031
600/300

(Continued)

FOREIGN PATENT DOCUMENTS

CN 101466299 A 6/2009
DE 102009046823 A1 11/2009
(Continued)

OTHER PUBLICATIONS

International preliminary report on patentability mailed Apr. 12, 2022, in PCT application No. PCT/EP2020/077795, (7 pgs).
(Continued)

*Primary Examiner* — Susan S Su
*Assistant Examiner* — Erin A Kim
(74) *Attorney, Agent, or Firm* — Michael North

(57) ABSTRACT

The invention relates to an arrangement and a software-based application for modifying an internal eye pressure in vivo, having modulating means for modifying the internal eye pressure and sensor means for capturing the internal eye pressure in vivo, and enabling easily operated and quickly reacting changes to the internal eye pressure while avoiding the disadvantages of the prior art, proposing that the modulating means are implemented for modifying the internal eye pressure as a function of the internal eye pressure captured by the sensor means.

7 Claims, 3 Drawing Sheets

Figure 1:
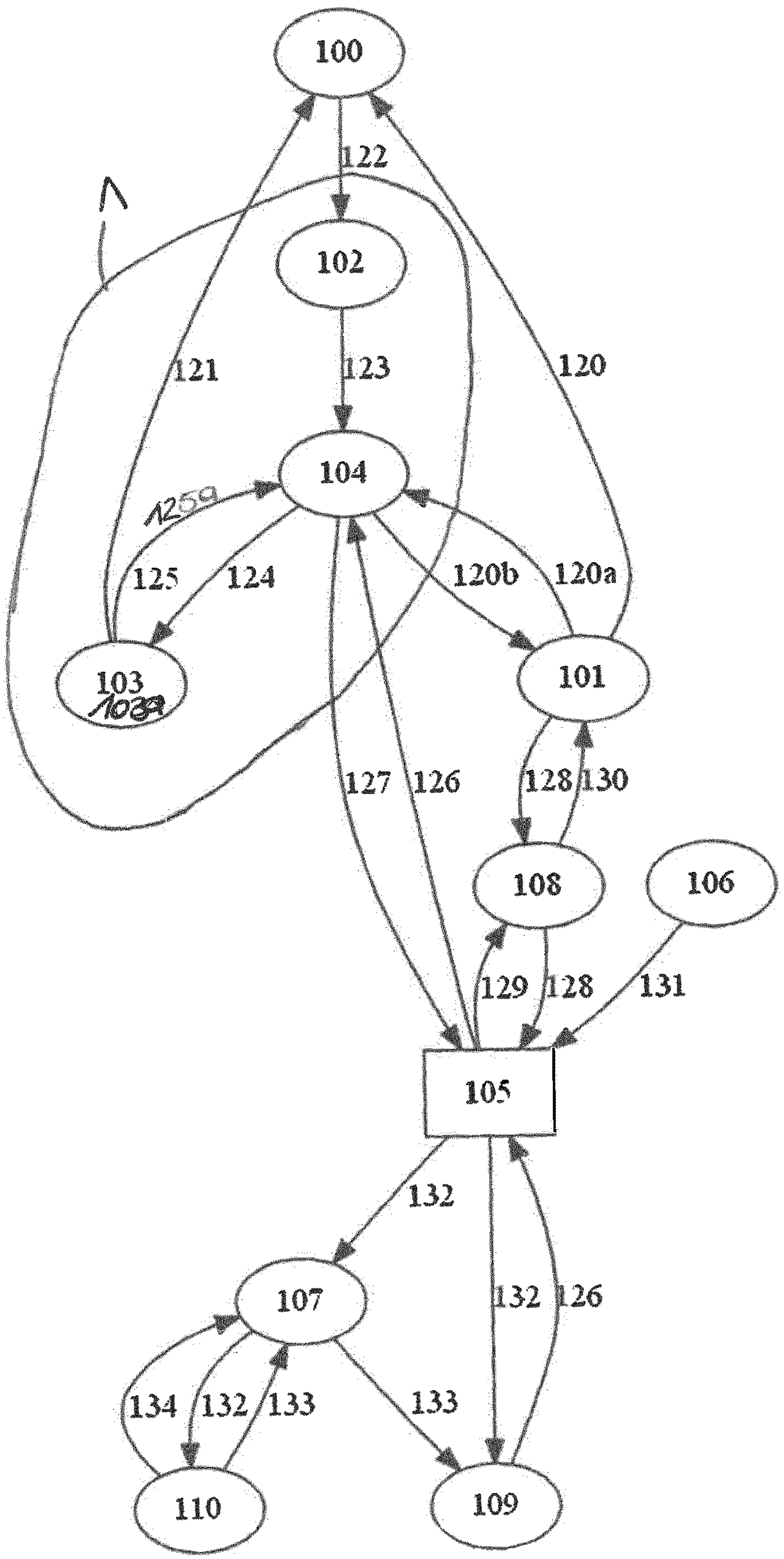

(58) Field of Classification Search
CPC . A61F 2250/0068; A61B 3/16; A61B 3/0033; A61B 5/03; A61B 5/6821
See application file for complete search history.

(56) References Cited

U.S. PATENT DOCUMENTS

| | | | | |
|---|---|---|---|---|
| 2012/0022506 | A1* | 1/2012 | Rickard | A61F 9/00781 604/66 |
| 2013/0090534 | A1 | 4/2013 | Burns et al. | |
| 2014/0275923 | A1 | 9/2014 | Haffner et al. | |
| 2019/0131009 | A1 | 5/2019 | Som et al. | |
| 2019/0147139 | A1 | 5/2019 | Roy et al. | |

FOREIGN PATENT DOCUMENTS

| | | | |
|---|---|---|---|
| DE | 102009046832 | A1 | 5/2011 |
| DE | 102017117657 | A1 | 2/2019 |
| JP | 2010517701 | A | 8/2008 |

OTHER PUBLICATIONS

International search report mailed Jan. 18, 2021, in PCT application No. PCT/EP2020/077795, (138 pgs).

* cited by examiner

ARRANGEMENT FOR MODIFYING AN INTERNAL EYE PRESSURE IN VIVO

CROSS-REFERENCE TO RELATED APPLICATIONS

This application is the US National Phase Under 371 of International Patent Application No. PCT/EP2020/077795, entitled "ARRANGEMENT FOR MODIFYING AN INTERNAL EYE PRESSURE IN VIVO", naming Stefan MEYER and Max OSTERMEIER as inventors, and filed Oct. 5, 2020, and to the German Patent Application No. 102019126959.8, entitled "ARRANGEMENT FOR MODIFYING AN INTERNAL EYE PRESSURE IN VIVO", naming Stefan MEYER and Max OSTERMEIER as inventors, and filed Oct. 8, 2019, the subject matter of which is hereby incorporated herein by reference.

The present invention relates to an arrangement for modifying an internal eye pressure in vivo, having modulating means for modifying the internal eye pressure and sensor means for capturing the internal eye pressure in vivo.

The invention further relates to a software-based application.

Such arrangements are used in the therapy of glaucoma patients. The objective of every glaucoma therapy is reducing internal eye pressure. An individual excessively high internal eye pressure is the cause of damage to the optic nerve and loss of vision. The necessity of effectively lowering the pressure has been proven by long-term studies and the individual determination of a target pressure at which progression of the disease is unlikely for the individual patient. Reducing the internal eye pressure can be done by means of medication or surgically, wherein the surgical approaches are partially supported by implants producing or maintaining an artificial outflow of vitreous humor.

Previous arrangements, particularly drainage implants having valves, for reducing the internal eye pressure have either a fixed drain cross section or can only be influenced externally, for example, by means of a magnet. This makes automatic regulation impossible, because manual intervention is always necessary. A disadvantage of prior arrangements having drainage implants or valves is that said arrangement cannot react, or reacts too slowly, to variations in the internal eye pressure and are difficult to use.

Against this backdrop, the object of the present invention is to disclose an arrangement of the type indicated above, as well as a method and a software-based application of the type indicated above, enabling improved treatment of variations in the internal eye pressure in case of glaucoma while avoiding the disadvantages of the prior art, and thereby being easy to use.

The arrangement according to the invention is intended to enable automatically feedback-controlled regulating of the internal eye pressure for glaucoma patients, and to enable telemetric system monitoring and remote controlled, corrective intervention by the ophthalmologist.

The object is achieved according to the invention with respect to the arrangement by a generic arrangement wherein the modulating means are implemented for modifying the internal eye pressure depending on the internal eye pressure captured by the sensor means. To this end, drainage implants having valves, for example, are used according to the invention in conjunction with internal eye pressure sensors having an integrated chip and a coil for transferring and processing data. The use of drug delivery systems for lowering the internal eye pressure by dispensing a pharmacological active substance is also conceivable. Furthermore, a combined use of drug delivery systems having drainage implants is also conceivable. Such a system enables automated therapy of patients having glaucoma. The use of a generic arrangement in telemedicine is thereby possible and patients need to visit an ophthalmologist less often.

In a preferred embodiment of the invention, the modulating means are implemented for dispensing across a surface at least one pharmacological active substance for modifying the internal eye pressure. Implantable drug delivery systems can be used for regulating. To this end, an electromechanical closing mechanism can expose a particular portion of a bioactive surface, across which a medication is released and dispensed to adjacent tissue. According to the invention, the remaining portion of the bioactive surface is covered by a membrane, for example, preventing dispensing of the medication to surrounding tissue. The portion of the surface covered by the membrane can be modified by the electromechanical closing mechanism, for example. The electromechanical closing mechanism can be regulated externally in one embodiment of the invention, so that automated regulating of the internal eye pressure is possible. Such drug delivery systems can be located in the tear duct, under the eyelid, or in subconjunctival, episcleral, intrascleral, or other locations in the eye. Rapid and direct and automated adjusting of the internal eye pressure is thereby advantageously achieved, without a physician needing to intervene. Variations in the internal eye pressure can thereby be captured more quickly and the optic nerve can be relieved. The risk of damage to the optic nerve of the patient is thereby reduced.

An advantageous embodiment of the invention comprises modulating means for modifying the area of the surface. For the medication dispensing systems used, for example, the area is modified across which the active substance is dispensed into the eyewash or the tear fluid. A precisely metered amount of the pharmacological active substance can thus be dispensed to the tear fluid or to the eyewash for reducing the internal eye pressure. The drug delivery system can have a connection for refilling the corresponding medication. Metering of the amount of medication dispensed to the eye is also thereby possible. Installing an electrically controlled valve in the infeed line to the dispensing surface is also conceivable, so that the amount arriving at the dispensing surface can be regulated. This makes personalized glaucoma therapy, customized to the individual patient, possible.

In an advantageous embodiment of the invention, the modulating means comprise means for modifying an outflow rate of the aqueous humor of an eye out of the eye. To this end, according to the invention, drainage implants having valves are implanted in the eye, for example. The opening state, particularly the opening cross section or opening angle of the valves, can be actuated and modified electronically, so that the valves can be actuated externally and the outflow of the aqueous humor can be regulated automatically. This opens up the possibility to drain aqueous humor in a selective manner in order to minimize the pressure on the optic nerve of the patient and to prevent further damage. The compatibility of such reducing of the internal eye pressure is very good in comparison with purely medicinal types of treatment.

In a preferred embodiment of the invention, the modulating means comprise drainage means for modifying an outflow rate of the aqueous humor out of the eye. To this end, drainage implants having a variable opening resistance, that is, having variable elasticity, for example, are used according to the invention. Very precise regulation of the outflow of aqueous humor is thereby possible. This makes it possible to capture daily or otherwise periodic variations in the internal eye pressure and to automatically compensate for the same on an individual patient basis. The use of such valves enables very precise adjusting of the internal eye pressure. Excessive eye pressure can thus be reduced quickly and automatically in that aqueous humor is drained. Altogether, automated adjusting of the internal eye pressure according to the invention increases the chances of successful therapy, as said chances are less dependent or not at all dependent on the individual patient complying with therapy.

An advantageous embodiment of the invention comprises data processing means provided for calculating a specified value relating to the internal eye pressure from values captured by the sensor means, wherein the modulating means are implemented for receiving the specified value from the data processing means. To this end, according to the invention, data transmitting channels similar to RFID are used and installed in the implants and the external reading devices, for example, and are able to receive and transmit information of the internal eye pressure sensor and the implanted valves or drug delivery systems. This makes possible the automated regulation of the internal eye pressure in a closed loop control circuit.

Based on the calculated values, predictions can be made about potential variations of the internal eye pressure and preventive measures can be taken in order to maintain the value constantly at the individual patient's value. The pressure on the optic nerve can thus be minimized and damage and associated further advancement of the glaucoma disease can be prevented.

In a preferred embodiment of the invention, the sensor means are implemented for wirelessly transferring information relating to the internal eye pressure to the modulating means and/or to the data processing means. To this end, according to the invention, RFID chips can be used and installed in the implants and the external reading devices, for example, and are able to receive and transmit information of the internal eye pressure sensor and the implanted valves or drug delivery systems. Thus information about the functional and structural state of the eye of the patient is thus available at all times. The patient thus regularly receives information about the state of the eye of the patient, without having to visit an ophthalmologist. This makes it possible, according to the invention, for the patient or optionally a physician to intervene in the regulating of the internal eye pressure.

In an advantageous embodiment of the invention, the modulating means are implemented for wirelessly transferring to the data processing means information relating to the modulating means. The individual patient information about the state, but particularly the opening cross section or opening resistance of the valves, can thus be provided at all times. Said information can be transmitted to the RFID chip, for example, installed in the external reading devices, and processed by means of an algorithm. The patient, a physician, or optionally a computer system based on an algorithm thus has the ability to evaluate the performance capacity of the arrangement at all times.

In a preferred embodiment of the invention, the data processing means are implemented for determining an individual patient specified value for the internal eye pressure using the individual patient information relating to the internal eye pressure. The external devices can read the measured parameters by means of an RFID chip and can determine a specified value for the patient by means of a saved algorithm. This makes possible the automated regulation of the internal eye pressure in a closed-loop control circuit. External intervention by the patient or a physician is thus no longer necessary, wherein correction by a user is possible at any time.

A preferred embodiment of the invention comprises data processing means implemented for determining by an operator an individual patient specified value for the internal eye pressure. External intervention by a physician or by the patient himself is possible at all times by means of an operator interface. Modifying of the weighting of the evaluating of the incoming information can thus be performed. For example, a specified value for the internal eye pressure is calculated manually by the physician and entered by means of the operator interface.

According to an advantageous embodiment of the invention, energy providing means for supplying the modulating means and/or the data processing means and/or the sensor means are provided for disposing outside of the eye. This can be a rechargeable battery or batteries, for example, installed in the external device. By means of the same, the implanted sensors and valves can be supplied with energy inductively. It is thus made possible that the sensors and valves are externally controlled by means of an electrical drive, without further batteries or battery systems needing to be implanted in the eye.

In an advantageous embodiment of the invention, the modulating means and/or the sensor means are implemented as nanoelectronic components. By using nanoelectric internal eye pressure sensors and valves, said components can be implanted in the eye in a very space-saving manner. The extent of surgical intervention for the patient is thus reduced. If the drainage systems should become clogged over time, or the performance of the valves and sensors should degrade, or in case of any complications that may arise, then said components can simply be removed and replaced. This increases acceptance of the form of therapy among patients.

The object of simpler handling of an arrangement for quickly reacting to variations of the internal eye pressure is achieved by a software-based application implemented for wirelessly communicating with modulating means for modifying the internal eye pressure and sensor means for capturing the internal eye pressure in vivo. Such an app can be installed on a handheld device of a patient, for example, and thus provide the patient with the ability to intervene in the regulating of the internal eye pressure. The patient thus advantageously needs to visit an ophthalmologist less frequently.

According to an advantageous embodiment of the invention, a software-based application is implemented for wirelessly receiving an internal eye pressure captured by sensor means for capturing internal eye pressure in vivo. Such an app is installed on the mobile terminal device of the patient, for example. By transmitting the data, the patient has access to the information about the state of the eye of the patient at all times. This demonstrably increases therapy compliance of the patient and saves visits to the ophthalmologist.

In an advantageous embodiment of the invention, the software-based application is implemented for calculating an individual patient specified value for an internal eye pressure from values captured by the sensor means. Such an app, for example, installed on a server and accessible and able to be parameterized from the computer of the physician or of the patient, calculates the internal eye pressure to be set for the individual patient so that no further damage to the optic nerve can occur. The physician or patient can see the calculated value by means of the app at all times, and thus has a better feeling for the state of the eye, or can optionally intervene by adjusting the specified value by means of the app. This enables automated, personalized therapy of glaucoma patients.

In a preferred embodiment of the invention, the software-based application is implemented for wirelessly transferring to the modulating means the specified value for the internal eye pressure of the individual patient. The individual specified value for the patient can thus be transmitted directly to the valve. By means of the electromechanical drive, a corresponding opening cross section can be exposed by means of the valve, so that aqueous humor can flow out and the internal eye pressure can be reduced. A closed-loop control circuit for regulating the internal eye pressure can thus be provided, substantially increasing the convenience to the patient having glaucoma.

In an advantageous embodiment of the invention, the software-based application is implemented for inputting and/or outputting information relating to an internal eye pressure. Such an app can be installed on a server, for example, and can be accessible from the mobile phone of the patient or of the physician. The patient is provided with all information about the state of the eye by means of the app. Furthermore, the physician or the patient can input a specified value deviating from the automatically calculated specified value and thus actively intervene in the closed control loop at any time. This makes it possible that the patient needs to visit a physician less often in order to set a corresponding specified value. The physician has the ability to treat patients remotely.

A preferred embodiment of the invention is described as an example with reference to a drawing, wherein further advantageous details can be seen in the figures of the drawing.

Functionally identical parts are thereby labeled with the same reference numeral.

The figures in the drawing show, in detail:

FIG. 1A schematic flowchart for regulating the internal eye pressure by means of an arrangement according to the invention, wherein the patient performs the measurements manually;

FIG. 2A schematic flowchart for regulating the internal eye pressure by means of an arrangement according to the invention, wherein the measurements are performed continuously and automatically; and FIG. 3A schematic flowchart for regulating the internal eye pressure by means of an arrangement according to the invention, wherein the available information is evaluated by a physician and compiled in a finding.

FIG. 1 shows a schematic flowchart of a control mechanism by means of an arrangement 1 according to the invention for automated regulating of the internal eye pressure. To this end, the internal eye pressure 122 is measured by the internal eye pressure sensor 102 implanted in the eye 100. Said measuring is performed either continuously or at defined points in time determined by the physician 110 or by the patient 101.

The raw data of the internal eye pressure sensor 123 is transferred to external devices 104, for example, having an RFID chip.

The external devices 104, for example, potentially mounted in multifunctional eyeglasses, a handheld device of the patient, or a pillow, actuate the valve 103 for regulating the internal eye pressure by means of a magnetic, thermal, acoustic, or optical signal 124. The opening cross section of the valve 103 or the opening resistance of the valve 103 is then modified in order to control the draining of the aqueous humor. The state, particularly the opening cross section 125 of the valve 103 or the opening resistance 125 of the valve 103, is transmitted back to the external device 104. The individual patient information 127, particularly the measured internal eye pressure 122, the opening cross section 125 of the valve 103 or the opening resistance 125 of the valve 103, is transmitted to a cloud-based database 105 and saved there.

An app according to the invention can be installed on a handheld device 104 of the patient, for example, by means of which the patient 101 can read or even influence the state of the valves 103.

The cloud-based database 105 has a patient portal 108 enabling access to the patient data 129 output by the cloud-based database 105. A patient diary 128 can be kept by means of the cloud-based database 105. The patient can enter data via the patient diary 128 for transmitting to medical personnel 110. According to the invention, the patient diary 128 can be entered by means of the app, on a mobile terminal device of the patient 101.

The cloud-based database 105 further comprises a physician access 107 by means of which the medical personnel obtain access to all prepared information 132.

The system further comprises an artificial intelligence present in an artificial intelligence module 109 (AI module) outside of the eye. The AI module 109 determines a specified value 126 for the internal eye pressure by means of an algorithm, taking into consideration the prepared information 132. Said specified value 126 can be overwritten at any time by medical personnel 110 by means of the physician access 107 and transferred to the AI module 109 as a modified specified value 133. The history 131 of the particular patient is saved in an external database 106, having information about the time curve of the internal eye pressure, as well as therapeutic and diagnostic information. The history 131 is transmitted to the cloud-based database 105, so that said information is taken into consideration when calculating the optimal internal eye pressure for the patient.

A manual measurement **120*a* is performed by the patient 101 in the control mechanism having an arrangement 1 according to the invention as shown in FIG. 1. The manual measurement 120*a* is manually initiated and automatically performed by means of an external device 104, for example, present in multifunctional glasses or a sleep mask. To this end, the internal eye pressure sensor 102** is actuated by means of an RFID chip.

The measured values **120*b*, particularly the internal eye pressure and the state of the valves 103 and the drainage systems 103, are transmitted to the external device 104 and provided to the patient 101 by means of the cloud-based database 105. An operator interface 130 is available to the patient 101 in the cloud-based database 105 for entering into the cloud-based database 105 the data of the patient diary 128 and the patient data 129 entered by the medical personnel 110**.

As shown in FIG. 1, all therapy data 120 is transferred to the external device 104 in order to thus produce a closed-loop control circuit between the internal eye pressure sensor 102, valve 103, and drainage system (103) and the information from the cloud-based database 105.

Figure 2:
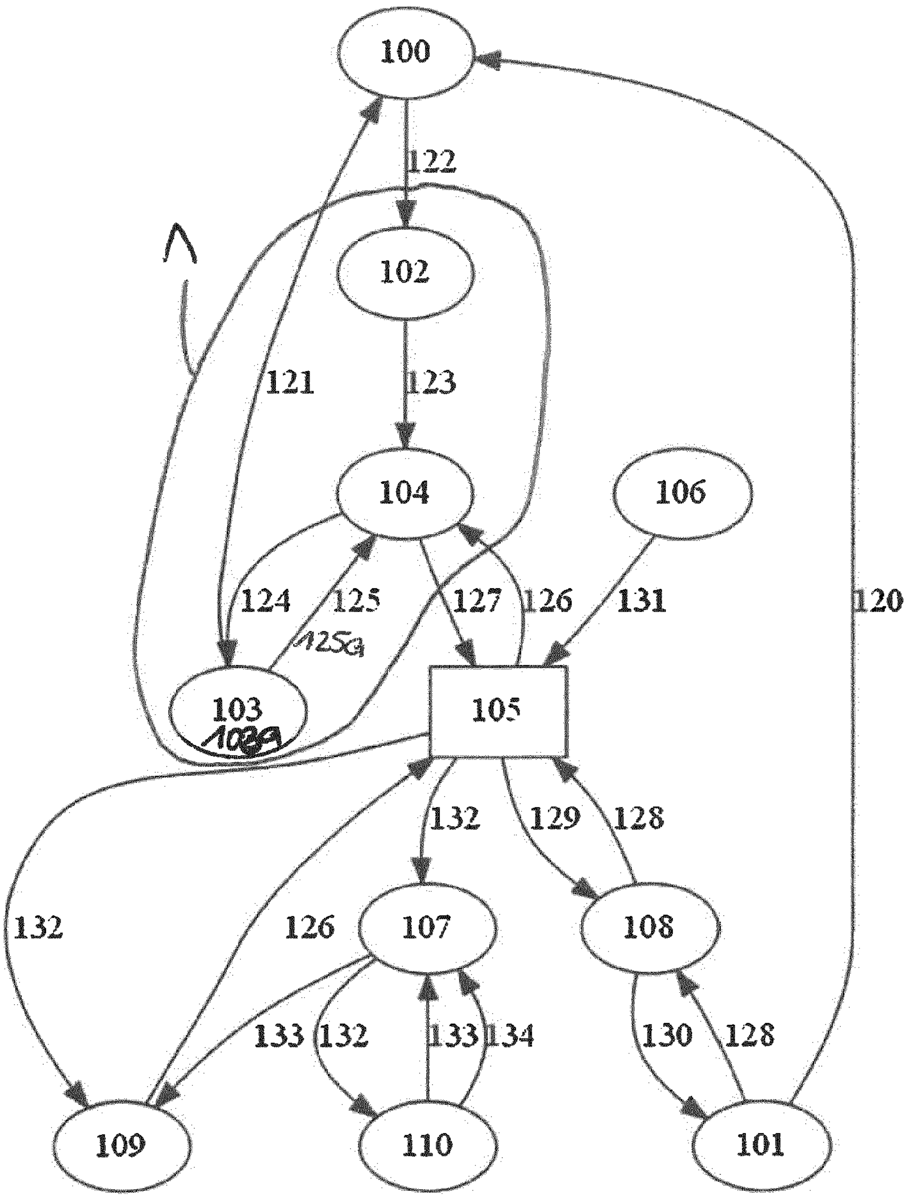

FIG. 2 makes clear that the measurements, unlike in the flowchart from FIG. 1, are not performed by the patient 101 but rather continuously and automatically, without action by the patient 101. To this end, a specified value 126 is transferred from the AI module 109 to the cloud-based database 105, for example, for transmitting the specified value 126 to the external device 104 and transmitting the specified value to a drug delivery system 103 by means of electronic data transmitting 124.

The drug delivery system 103 is implemented such that the area of the surface can be modified across which a pharmacological active substance can be dispensed. A precisely metered amount of the pharmacological active substance 121 for modifying the internal eye pressure can thus be dispensed to the eyewash and the internal eye pressure thus modified. The information about the state of the drug delivery system 125*a*, particularly the portion of the area of the bioactive surfaces covered by the membrane and the portion of the area not covered by the membrane, can be transmitted to the handheld device of the patient by means of a Bluetooth interface, for example.

The AI module 109 receives a guideline value 133 from the physician access 107 for calculating the specified value 126 for the individual patient. By means of said physician access 107, the physician 110 can intervene at any time and can specify a corresponding guideline value 133 and thus override the specified value 126 determined by the AI module 109. To this end, an app according to the invention can be installed on the PC of the physician 110, for example. The physician 110 can also enter a response 134 to the patient 101 for issuing to the patient 101 by means of the cloud-based database 105, so that communication between the physician 110 and the patient 101 is possible. Because the data transmitting functions by means of Wi-Fi, Bluetooth, or a WWAN interface, it is not necessary that the physician 110 and patient 101 are present at the same location, so that the use of the drug delivery systems 103 or valves 103 is possible in telemedicine in conjunction with the internal eye pressure sensor 102.

As shown in FIG. 2, the information of the patient diary 128 is transmitted to the cloud-based database 105 by means of the patient access 108 and is forwarded both to the AI module 109 in the form of prepared information 132 as a calculation basis, and to the physician access 107 for monitoring.

The app, for example, installed on the handheld device 104 of the patient, can be used according to the invention for displaying the prepared information 132.

Figure 3:
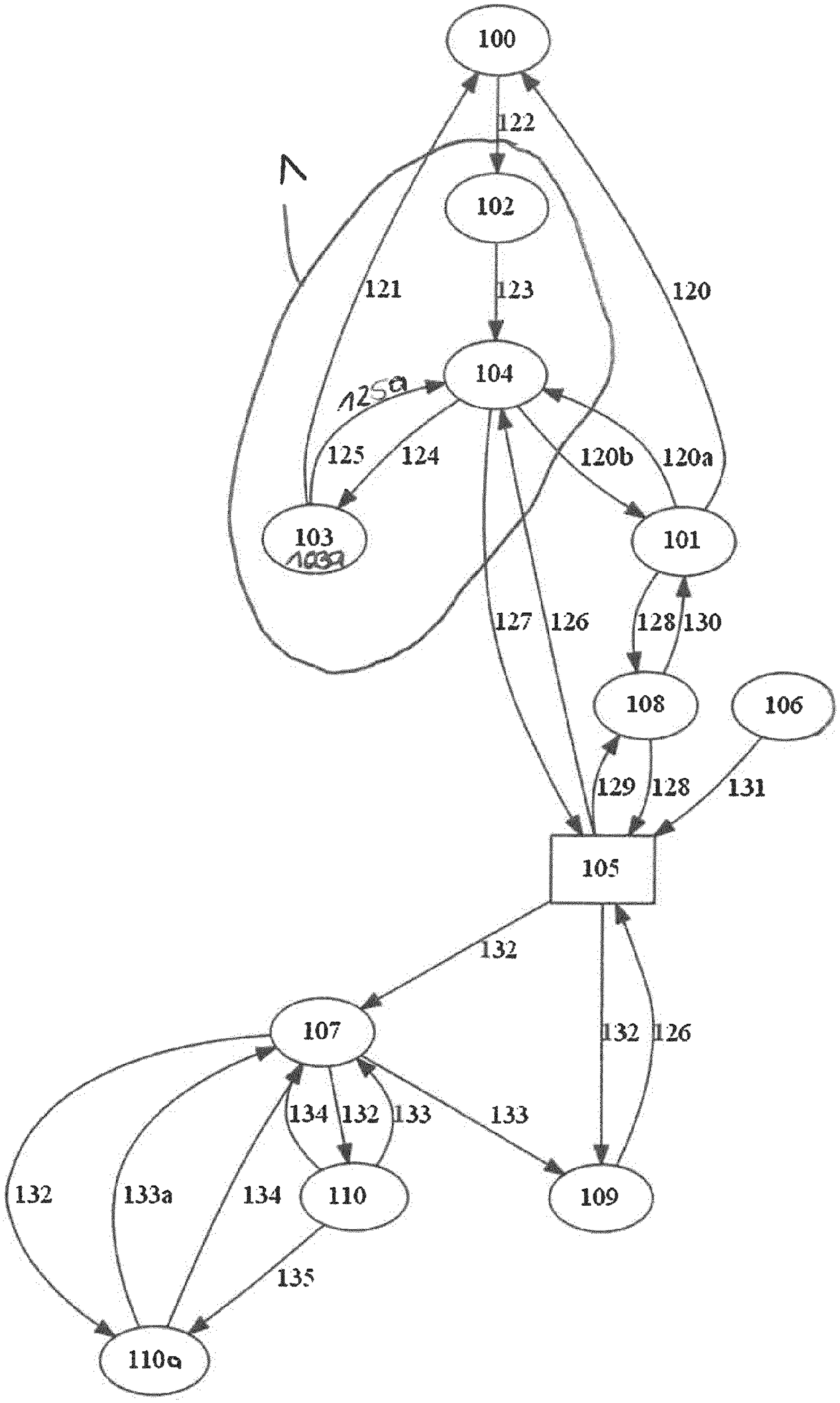

FIG. 3 shows a schematic flowchart of a closed-loop control mechanism having an arrangement 1 according to the invention for regulating an internal eye pressure, wherein a physician 110, particularly a telemedicine physician 110, communicates with the AI module 109 and can overwrite the specified value 126 calculated by the AI module 109 with his own or a medical guideline value 133.

FIG. 3 makes clear that the system provides the possibility for a second physician or telemedicine physician 110*a* to enter a further guideline value 133*a* and that said value is also taken into consideration for determining the specified value 126. It is thus possible to obtain a second opinion in the field of telemedicine.

FIG. 3 shows that, to this end, a finding 135 having a corresponding recommendation for therapy is transmitted from the first physician or telemedicine physician 110 to a second physician or telemedicine physician 110*a*. The second physician or telemedicine physician 110*a* can transmit a second guideline value 133 to the patient 101 by means of the physician access 107 and the cloud-based database 105.

FIG. 3 shows that the processes for transmitting the specified value 126 to the valve 103 are identical to those already explained in FIG. 1 and FIG. 2. It is conceivable to combine a system having valves 103 and a drug delivery system 103 as a high level of effectiveness and very good patient 101 compatibility is thereby evident.

LIST OF REFERENCE NUMERALS

1 Arrangement
100 Eye
101 Patient
102 Internal eye pressure sensor
103 Valve
103*a* Drug delivery system
104 External device
105 Cloud-based database
106 External databases
107 Physician access
108 Patient access
109 AI module
110 Physician
110*a* Physician 2
120 Therapy information
120*a* Manual measurements
120*b* Measured values
121 Pharmacological active substance
122 Internal eye pressure
123 Raw data of the internal eye pressure sensor
124 Electronic data transmission
125 State of the valve
125*a* State of the drug delivery system
126 Specified value
127 Individual patient information
128 Patient diary
129 Patient data
130 Operator interface
131 Patient history
132 Prepared information
133 Guideline value
133*a* Guideline value 2
134 Feedback to the patient
135 Findings

The invention claimed is:

1. A system for in vivo adjustment of internal eye pressure, the system comprising:

one or more modulating means for modifying an internal eye pressure;

one or more sensors for capturing the internal eye pressure in vivo, the one or more modulating means modify the internal eye pressure as a function of the internal eye pressure that has been captured by the one or more sensors; and an artificial intelligence module (AI module) outside of the eye, the AI module is implemented to determine a specified value for the internal eye pressure by means of an algorithm, taking into consideration information specific to a patient and relating to the internal eye pressure;

wherein the one or more modulating means comprise a drug delivery system implemented for dispensing across a surface at least one pharmacological active substance for modifying the internal eye pressure and implemented for modifying an area of the surface, the surface is an exposed portion of a bioactive surface, across which the pharmacological active substance is released and dispensed to an adjacent tissue;

wherein the one or more modulating means comprise one or more drainage means that modify an outflow rate of aqueous humor from an eye.

2. The system according to claim 1, further comprising one or more data processing devices that perform steps comprising:

in response to receiving values captured by the one or more sensors, determining a specified value relating to the internal eye pressure; and providing the specified value to the one or more modulating means.

3. The system according to claim 2, wherein the one or more sensors wirelessly transfer data relating to the internal eye pressure to at least one of the one or more modulating means or the one or more data processing devices.

4. The system according to claim 2, wherein the one or more modulating means wirelessly transfer data relating to the one or more modulating means to the one or more data processing devices.

5. The system according to claim 2, wherein the one or more data processing devices are user-configurable.

6. The system according to claim 2, further comprising one or more energy sources disposed outside of the eye, one or more energy sources supplying to at least one of the one or more modulating means, the one or more data processing devices, or the one or more sensors.

7. The system according to claim 1, wherein at least one of the one or more modulating means or the one or more sensors comprise one or more nanoelectronic components.

* * * * *